(12) United States Patent
Paul et al.

(10) Patent No.: US 7,306,580 B2
(45) Date of Patent: Dec. 11, 2007

(54) MEDICAL DEVICE WITH THERAPEUTIC AGENTS

(75) Inventors: Ram H. Paul, Bloomington, IN (US); Daniel J. Sirota, Bloomington, IN (US); Paul D. Amarant, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 596 days.

(21) Appl. No.: 10/414,939

(22) Filed: Apr. 16, 2003

(65) Prior Publication Data

US 2004/0210208 A1 Oct. 21, 2004

(51) Int. Cl.
A61M 5/00 (2006.01)
A61M 5/32 (2006.01)
A61M 25/00 (2006.01)

(52) U.S. Cl. ...................... 604/264; 604/523

(58) Field of Classification Search ................ 604/263, 604/264, 523, 507; 623/1.13, 1.49, 1.42
See application file for complete search history.

(56) References Cited

U.S. PATENT DOCUMENTS

| | | | |
|---|---|---|---|
| 3,625,214 A | 12/1971 | Higuchi | |
| 3,926,188 A | 12/1975 | Baker et al. | |
| 4,107,121 A | 8/1978 | Stoy | |
| 4,442,133 A | 4/1984 | Greco et al. | |
| 4,678,660 A | 7/1987 | McGary et al. | |
| 4,749,585 A | 6/1988 | Greco et al. | |
| 4,895,566 A | 1/1990 | Lee | |
| 4,917,686 A | 4/1990 | Bayston et al. | |
| 4,952,419 A | 8/1990 | DeLeon et al. | |
| 5,360,397 A | 11/1994 | Pinchuk | |
| 5,362,754 A | 11/1994 | Raad et al. | |
| 5,520,664 A | 5/1996 | Bricault, Jr. et al. | |
| 5,624,704 A | 4/1997 | Darouiche et al. | |
| 5,688,516 A | 11/1997 | Raad et al. | |
| 5,902,283 A | 5/1999 | Darouiche et al. | |
| 6,299,604 B1 * | 10/2001 | Ragheb et al. | 604/265 |
| 6,663,662 B2 * | 12/2003 | Pacetti et al. | 623/1.13 |
| 2002/0107506 A1 | 8/2002 | McGuckin, Jr. et al. | |
| 2002/0121282 A1 | 9/2002 | McGuckin, Jr. et al. | |

FOREIGN PATENT DOCUMENTS

| | | |
|---|---|---|
| CH | 649 916 A5 | 6/1985 |
| WO | WO 98/35717 A1 | 8/1998 |

* cited by examiner

Primary Examiner—Kevin C. Sirmons
Assistant Examiner—Elizabeth MacNeill
(74) Attorney, Agent, or Firm—Brinks Hofer Gilson Lione

(57) ABSTRACT

A medical device is adapted for at least partial implantation into a body and includes first and second sections along the length of the device. A first therapeutic agent is associated with the first section and a second therapeutic agent is associated with the second section. The first therapeutic agent can be one or more antiproliferative, such as paclitaxel, a paclitaxel derivative, or a paclitaxel pro-drug, anticoagulant, antithrombotic, thrombolytic, fibrinolytic, or combination thereof. The second therapeutic agent can be one or more antimicrobials, such as one or more antibiotics. Each of the first and second therapeutic agents can either be posited on one or more surfaces of the respective section, or impregnated within the section. The device can include a separator to space the first and second sections. A method of making a medical device and a method of establishing access to a vessel within a body are also provided.

22 Claims, 9 Drawing Sheets

MEDICAL DEVICE WITH THERAPEUTIC AGENTS

FIELD OF THE INVENTION

The present invention relates to medical devices suitable for at least partial implantation into a body. More specifically, the present invention relates to medical devices with therapeutic agents. In preferred embodiments, the invention relates to cannulae, such as catheters, with therapeutic agents. The present invention also relates to a method of making a medical device, and a method of establishing access to a vessel within a body.

BACKGROUND OF THE INVENTION

Many types of medical devices are used in a variety of medical procedures that include at least partial implantation into a body. When implanted, medical devices can be in intimate contact with a variety of cells, tissues, and body systems. For example, cannulae, such as catheters, are used in a variety of medical procedures to introduce articles, such as stents, into body vessels. Cannulae are also used to establish a communicative passageway by which a body vessel can be accessed from the exterior of the body. These cannulae are indispensable in procedures that require repeated access to the vessel, such as hemodialysis procedures that include repeated extracorporeal treatment of blood.

While implanted medical devices provide several advantages, they also present an opportunity for infection. Indwelling medical devices, such as indwelling cannulae used for access ports, are particularly susceptible to infection due to their long term presence in the body. In essence, the cannula provides a path from the external environment into the body along which microorganisms can colonize, and eventually produce an infection.

The establishment of an infection can require intervention, such as treatment with a therapeutic agent or even mechanical manipulation of the medical device to remove the microorganisms. Even worse, the infection may require removal and replacement of the medical device. Ultimately, the presence of an infection may outweigh the benefits of the implantation.

Infections associated with indwelling medical devices are commonly caused by bacteria or fungi. The most common organisms associated with infections associated with indwelling devices are *Staphylococcus epidermidis* and *Staphylococci aureus*. *Candida albicans*, a fungi, is another significant cause of infections associated with these devices. No matter the microorganism, establishment of infection requires colonization along the surface of the medical device, which depends on a variety of factors, including the formation of glycocalyx and a fibrin sheath.

Glycocalyx is a polysaccharide produced by adherent microorganisms. The glycocalyx allows the microorganisms to adhere to the surface, and contributes to the formation of a biofilm around the medical device. In addition to the glycocalyx formation, a fibrin sheath is often produced by the host as a natural result of thrombogenesis. The fibrin sheath essentially covers the surfaces of the indwelling device, and provides another agent onto which microorganisms can adhere.

Considering the importance of implantable medical devices, considerable attention has been directed toward preventing colonization and/or infection on these articles. The art contains many examples of medical devices that incorporate a variety of approaches that attempt to control colonization and/or infection. For example, U.S. Pat. No. 5,688,516 to Raad et al. discloses medical devices coated with mixtures of antibiotics and other therapeutic agents. Also, U.S. Pat. No. 5,624,704 to Darouiche et al. discloses medical devices impregnated with antimicrobials.

As indicated above, the microorganisms commonly associated with colonization and/or infection from implanted medical devices typically originate from outside the body, such as on the skin, and progress into the body along the path of the medical device. Once inside the body, the microorganisms produce the glycocalyx that facilitates adherence, and the body produces a fibrin sheath around the device that facilitates colonization and establishment of an infection. Thus, two distinct processes are occurring on two distinct portions of the medical device. Outside the body, microorganisms gain access to the device and begin to proceed into the body. Inside the body, microorganisms arriving from the external portion of the device produce a glycocalyx to facilitate adherence, and the body produces the fibrin sheath which further facilitates adherence. The prior art fails to recognize the localization of these processes in the available devices designed to prevent or inhibit colonization and/or infection.

BRIEF SUMMARY OF THE INVENTION

The present invention provides a medical device for at least partial implantation in a body, such as a human body, comprising a main body having a first end, a second end, and a length extending from the first end to the second end. The medical device has first and second sections extending along the length of the medical device. The first section is near the first or distal end of the device and the second section is near the second or proximal end of the device. The first section has a first therapeutic agent, and the second section has a second therapeutic agent. Once implanted, the first section is fully implanted in the body, and the second section is only partially implanted in the body. The second section is at least partially positioned within a subcutaneous layer of the body, and may have a section that extends outside of the body.

In a preferred embodiment, the main body comprises a cannula having an interior surface and an exterior surface. The cannula defines a lumen. Further, the medical device can include a separator that separates the first section from the second section.

The first and second therapeutic agents can be associated with the first and second sections, respectively, in a variety of manners. For example, the agents can be impregnated into the main body of the medical device, or can be posited onto the medical device. In a preferred embodiment, one or more of the therapeutic agents is coated onto one or more surfaces of the medical device. In a particularly preferred embodiment, the first therapeutic agent is impregnated into the first section of the main body and the second therapeutic agent is coated onto at least one surface of the second section of the main body.

The first and second therapeutic agents can be any suitable type of agent. Examples of suitable types of agents include, without limitation, antiproliferatives, anticoagulants, antithrombotics, thrombolytics and/or fibrinolytics, and antimicrobials.

In a preferred embodiment, a first therapeutic agent comprises an antiproliferative. Particularly preferable, the first therapeutic agent comprises paclitaxel, a paclitaxel derivative, or a paclitaxel pro-drug. Also preferable, the second therapeutic agent comprises one or more antimicrobials. The antimicrobial can be an antibiotic, an antiseptic, and/or a disinfectant. In a particularly preferred embodiment, the second therapeutic agent comprises a blend of two or more antibiotics. A desirable blend includes rifampin and minocycline.

The present invention also provides a method of making a medical device for at least partial implantation. The method comprises providing a main body having a first end, a second end, a length extending from the first end to the second end, a first section along the length, and a second section along the length; exposing the first section to a solvent so that the first sections swells; soaking the first section in a solution containing a first therapeutic agent; drying the first section; and coating at least a portion of the second section with a second therapeutic agent.

The present invention also provides a method of establishing access to a vessel of the body. The method comprises providing a medical device comprising a cannula having a distal end, a proximal end, an interior surface, an exterior surface, and defining a lumen. The cannula has a length extending from the proximal end to the distal end, a first section extending along the length with a first therapeutic agent, and a second section extending along the length with a second therapeutic agent. The method also includes implanting the distal end of the cannula into the body so that the proximal end remains either substantially outside the body or in a subcutaneous layer, and forming an interface between the distal end and the vessel. The interface can be a direct insertion of the distal end into the vessel or an attachment of the distal end to the vessel, such as an anastomosis.

DETAILED DESCRIPTION OF THE INVENTION

Medical devices according to the present invention can be any of a variety of medical device types and configurations. The medical device need only be at least partially implantable within a body. Examples of types of medical devices that can be made according to the present invention include leads, fasteners, and cannula, such as catheters.

Figure 1:
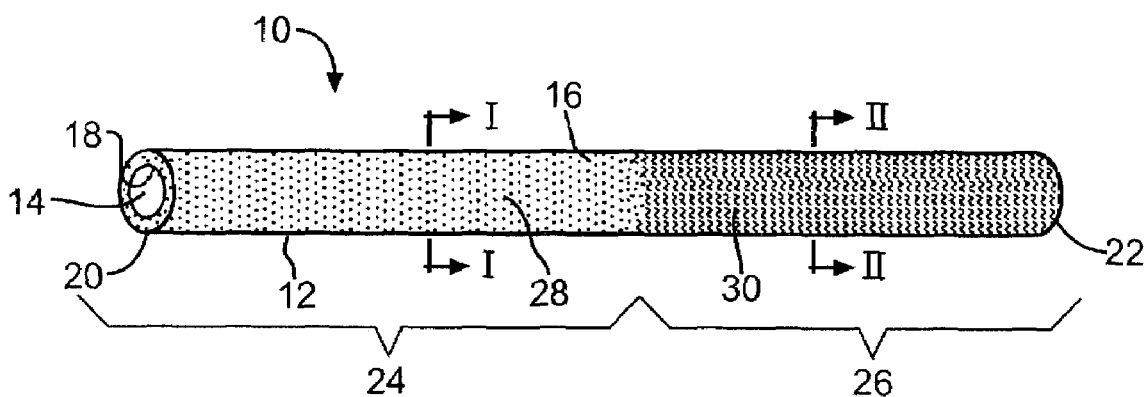
FIG. 1 is a schematic illustration of a medical device according to an embodiment of the present invention.
Figure 1A:
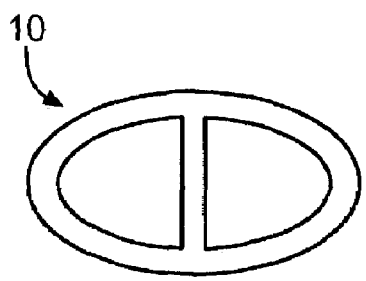
FIGS. 1A, 1B, 1C and 1D illustrate various cross-sectional shapes and lumen configurations for devices according to the present invention.
Figure 1B:
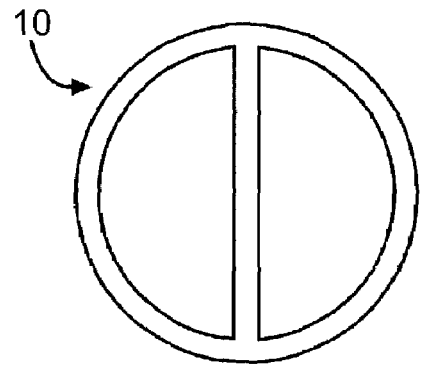
Figure 1C:
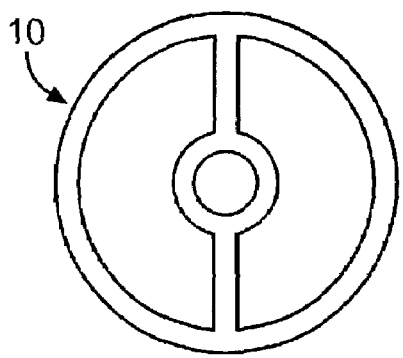
Figure 1D:
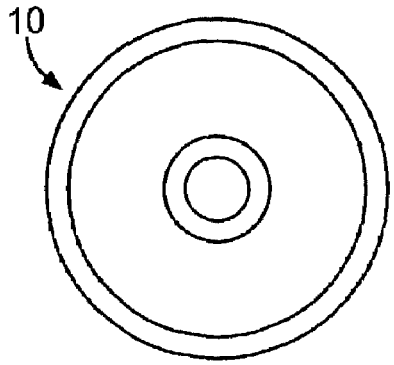

FIG. 1 illustrates a medical device according to one embodiment of the present invention. In this embodiment, the medical device 10 comprises a cannula having a main body 12 and defining a lumen 14. The cannula 10 has exterior 16 and interior 18 surfaces, a first or distal end 20, and a second or proximal end 22.

The length of the cannula extends from the first end 20 to the second end 22. A first section 24 of the cannula 10 extends along a portion of the length, and a second section 26 extends along another axially distinct portion of the length. Both the first 24 and second 26 sections extend circumferentially around the cannula 10 and axially along a respective portion of the length. As illustrated in the figures the first section 24 is preferably near the first end 20 and the second section 26 is preferably near the second end 22.

Figure 2:
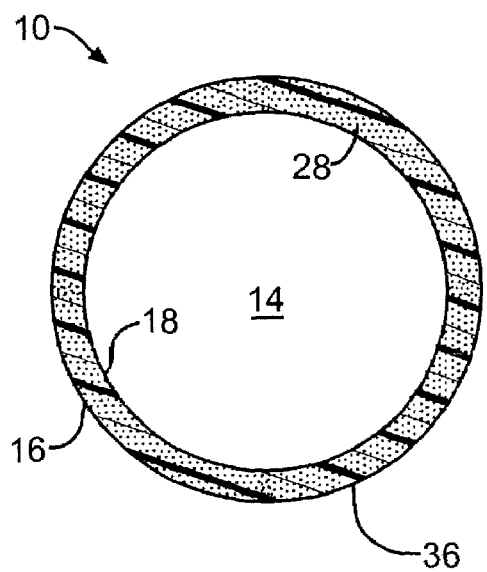
FIG. 2 is a cross-sectional view taken along line I-I in FIG. 1.
Figure 6:
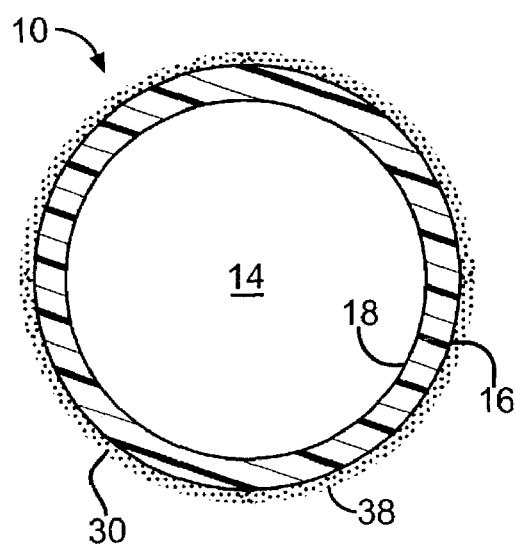
FIG. 6 is a cross-sectional view taken along line II-II in FIG. 1.

A first therapeutic agent 28 is associated with the cannula 10 at the first section 24, and a second therapeutic agent 30 is associated with the cannula 10 at the second section 26. Both the first 28 and second 30 therapeutic agents can be associated with the cannula 10 in a variety of manners. Preferably, as illustrated in FIG. 2, the first therapeutic agent 28 comprises an impregnated agent 36 disposed in the material of the first section 24, such as by bulk distribution, solvent swelling, or other suitable techniques. Also, as illustrated in FIG. 6, the second therapeutic agent 30 preferably comprises a coating layer 38 posited on the external surface 16 of the second section 26 of the cannula 10.

Figure 3:
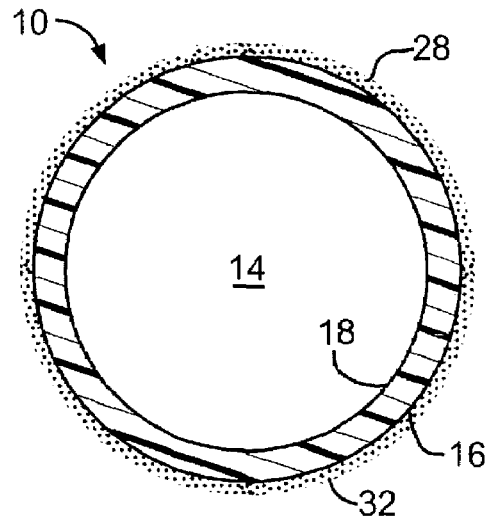
FIG. 3 is a cross-sectional view illustrating an embodiment of the present invention.
Figure 4:
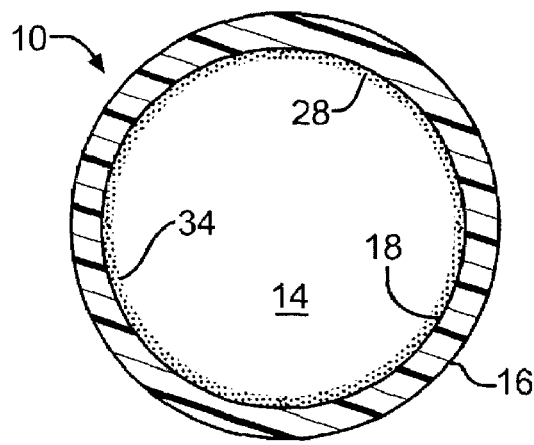
FIG. 4 is a cross-sectional view illustrating an embodiment of the invention.
Figure 5:
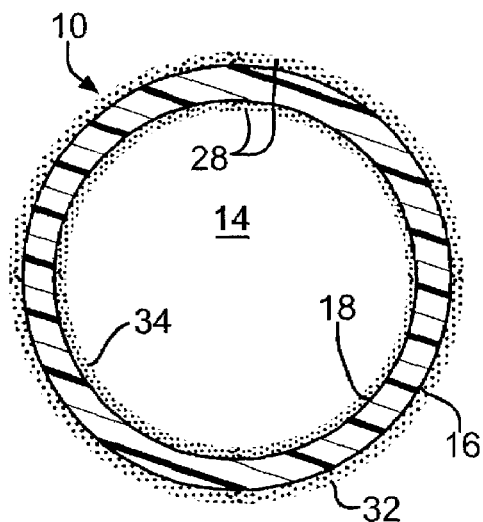
FIG. 5 is a cross-sectional view illustrating an embodiment of the invention.
Figure 7:
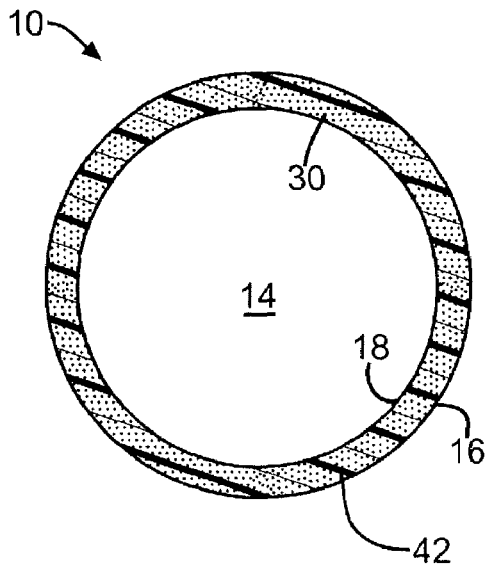
FIG. 7 is a cross-sectional view illustrating an embodiment of the invention.
Figure 8:
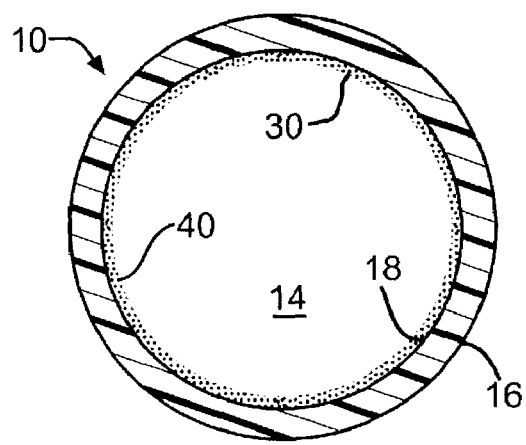
FIG. 8 is a cross-sectional view illustrating an embodiment of the invention.
Figure 9:
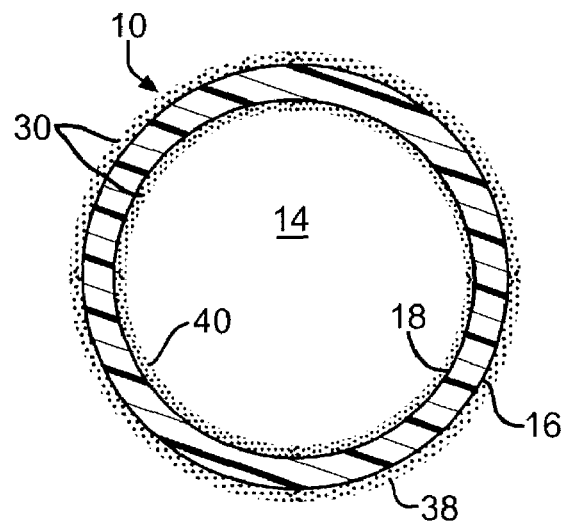
FIG. 9 is a cross-sectional view illustrating an embodiment of the invention.

Many alternative arrangements for the first 28 and second 30 therapeutic agents are within the scope of the present invention. For example, FIGS. 3-5 illustrate alternative arrangements for the first therapeutic agent 28 in relation to the first section 24 of the cannula 10, and FIGS. 7-9 illustrate alternative arrangements for the second therapeutic agent 30 in relation to the second section 26 of the cannula 10. As illustrated in FIG. 3, the first therapeutic agent 28 can comprise a coating layer 32 posited on the external surface 16 of the cannula 10. As illustrated in FIG. 4, the first therapeutic agent 28 can comprise a coating layer 34 posited on the internal surface 18 of the cannula 10. Also, as illustrated in FIG. 5, the first therapeutic agent 28 can comprise a coating layer 32 posited on the external surface 16 and a coating layer 34 posited on the internal surface 18. The second therapeutic agent 30 can likewise be associated with the second section 26 in similar ways. Thus, as illustrated in FIG. 7, the second therapeutic agent 30 can comprise an impregnated agent 42 disposed in the material of the second section 26 of the cannula 10. As illustrated in FIG. 8, the second therapeutic agent 30 can comprise a coating layer 40 posited on the interior surface 18 of the cannula 10. Furthermore, as illustrated in FIG. 9, the second therapeutic agent 30 can comprise a coating layer 38 posited on the external surface 16 and a coating layer 40 posited on the internal surface 18.

In addition to the various arrangements for each of the first 28 and second 30 therapeutic agents, any suitable combination of arrangements, i.e., one for each agent 28, 30, can be utilized.

The main body 12 can be formed of any suitable material, and need only be biocompatible and appropriate for the desired type of medical procedure in which the device will be utilized. Preferred materials for the main body 12 include thermoplastic and thermoset materials. In particularly preferred embodiments, silicone, a thermoset material, is utilized as the material of the main body 12.

The cross-sectional shape of the medical device can be any shape suitable for the types of procedures in which the device will be utilized. A circular cross-sectional shape is particularly preferable in embodiments in which the device comprises a cannula, such as that illustrated in FIG. 1. A circular cross-sectional shape maximizes space within the lumen 14 of the cannula 10 while also providing a suitable shape for interfacing with a body vessel. Furthermore, the medical device can have any suitable configuration of lumen(s), and the chosen configuration will depend on the application for which the device is used. Single and multi-lumen configurations can be utilized. FIGS. 1A, 1B, 1C and 1D illustrate various suitable cross-sectional shapes and lumen configurations for use in medical devices 10 according to the present invention.

The first 28 and second 30 therapeutic agents can be any suitable agents, and need only provide the desired effects. Thus, the first therapeutic agent 28, which is associated with the first section 24 near the first or distal end 20, need only have a negative effect on the formation of fibrin sheaths. Also, the second therapeutic agent 30, which is associated with the second section 26 near the second or proximal end 22, need only have an antimicrobial effect.

Examples of suitable therapeutic agents for use as the first therapeutic agent 28 include anticoagulants, antithrombotics, thrombolytics and/or fibrinolytics, and antiproliferatives. The type of agent selected as the first therapeutic agent 28 will depend on several factors, including the stage of development of the fibrin sheath at which interference with further development is desired. For example, antithrombotics, such as heparin, hirudin, hirulog and PPACK, directly or indirectly bind thrombin to prevent polymerization of fibrin from fibrinogen, a necessary step in the coagulation process. Anticoagulants, such as the glycoprotein IIbIIIa inhibitors, attach to platelet receptors and block activation sites, thereby preventing their degranulation and release of serotonin. Other anticoagulants block ADP induced platelet aggregation, such as Ticlopidine and Clopidigrel. Still other anticoagulants such as warfarin and coumadin inhibit the action of vitamin K and the production of coagulation factors. Some anticoagulants, such as aspirin, inhibit platelet aggregation by inhibiting Thromboxane A2.

Thrombolytics and/or fibrinolytics lyse or break down an organized thrombus by activating plasmin, which breaks down fibrin. Examples of suitable thrombolytics and/or fibronolytics include Tissue Plasminogen Activator (tPA), Urokinase, and Streptokinase.

Certain matrix metalloproteinases, such as collagenase, can break down the connective tissue of a formed fibrin sheath.

Examples of suitable antithrombotics include heparin, hirudin, hirulog, and PPACK. Examples of suitable anticoagulants include glycoprotein IIbIIIa inhibitors, ticlopidine, clopidigrel, warfarin, coumadin, and aspirin. Examples of suitable thrombolytics and/or fibrinolytics include tPA, recombinant tPA, urokinase, streptokinase, Tenecteplase, Alteplase, Activase, Lysatec, Antistreplase, APSAC, Eminase, Retaplase, Retavase, Hannahpep (Indian King Cobra venom), and Ancrod (Malayan pit viper venom). Examples of suitable matrix metalloproteinases include collagenase. Other suitable agents for the first therapeutic agent include olyeyloxyethyl phosphorylcholine.

Also, combinations of two or more agents can be used as the first therapeutic agent 28.

In a preferred embodiment, the first therapeutic agent comprises an antiproliferative. In a particularly preferred embodiment, the first therapeutic agent 28 comprises natural or synthetic paclitaxel, a derivative of paclitaxel, and/or a paclitaxel pro-drug.

Paclitaxel is a natural diterpere product isolated from the Pacific yew tree (*Taxus brevifolia*). Paclitaxel is a member of the taxane family of terpenes, and was first isolated by Wani et al. (*J. Am. Chem. Soc.*, 93:2325, 1971). Paclitaxel has proven efficacious in the treatment of a variety of neoplasms, and has been approved for use in the clinical treatment of breast and ovarian cancer in the United States.

Paclitaxel functions as an antiproliferative agent; i.e., as an inhibitor of cell replication. It is believed that paclitaxel inhibits replication by inducing an abnormal polymerization of tubulin. This results in stabilization of microtubules and disruption of the cell division process, mitosis. Further, paclitaxel inhibits smooth muscle cell proliferation both in vitro and in vivo.

Paclitaxel can be used in medical devices of the present invention in its basic form, as a derivative (see for example U.S. Pat. No. 6,476,242 to Kingston et al. for 2-AROYL4-ACYL PACLITAXEL ANALOGS; see also U.S. Pat. No. 6,441,025 to Li et al. for WATER SOLUBLE PACLITAXEL DERIVATIVES), and/or as a PRO-DRUG (i.e., a drug that yields paclitaxel upon action by an appropriate agent, such as a naturally occurring enzyme; see U.S. Pat. No. 6,153,756 to Digenis et al. for SOLUBLE PRODRUGS OF PACLITAXEL). Also, a preparation of paclitaxel can be utilized. Any suitable preparation can be used, and should facilitate placement of the paclitaxel into or on the medical device of the present invention, and should allow its release from the medical device. Examples of suitable paclitaxel preparations include those described in U.S. Pat. No. 5,681,846 to Triysel for EXTRUDED STABILITY FORMULATIONS FOR PACLITAXEL.

Considerable attention has been directed toward the effects of paclitaxel on a variety of cell types and physiological processes. Paclitaxel may arrest the migration of fibroblasts and smooth muscle cells, thereby reducing or preventing connective tissue formation that often follows fibrin sheath formation. It has also been found to decrease restenosis of human coronary arteries following stent use.

The second therapeutic agent 30 can be any suitable antimicrobial agent. As used herein, the term 'antimicrobial' means any agent that has killing or growth inhibiting effects on one or more microorganisms.

Suitable classes of antimicrobials include antibiotics, disinfectants, and antiseptics.

In a preferred embodiment, the second therapeutic agent 30 comprises one or more antibiotics having activity against the common microorganisms associated with colonization and/or infection with indwelling cannulae. Examples of suitable classes of antibiotics include tetracyclines, rifamycins, macrolides, penicillins, cephalosporins, other beta-lactam antibiotics, aminoglycosides, chloramphenicol, sulfonamides, glycopeptides, quinolones, fusidic acid, trimethoprim, metronidazole, clindamycin, mupirocin, polyenes, azoles and beta-lactam inhibitors.

Examples of specific antibiotics that can be used as the second therapeutic agent 30 include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin.

The second therapeutic agent 30 can comprise a combination of two or more antimicrobials. In these embodiments, the two or more antimicrobials can be located in or on discrete locations within the second section 26, or the two or more antimicrobials can be blended together and uniformly distributed within or on the second section 26.

In a preferred embodiment, rifampin and minocycline are used as the second therapeutic agent 30. The rifampin and minocycline preferably are blended together and evenly distributed either in or on the second section 26. In a particularly preferred embodiment, discussed below, blended rifampin and minocycline are coated onto the surfaces of second section 26.

Figure 10:
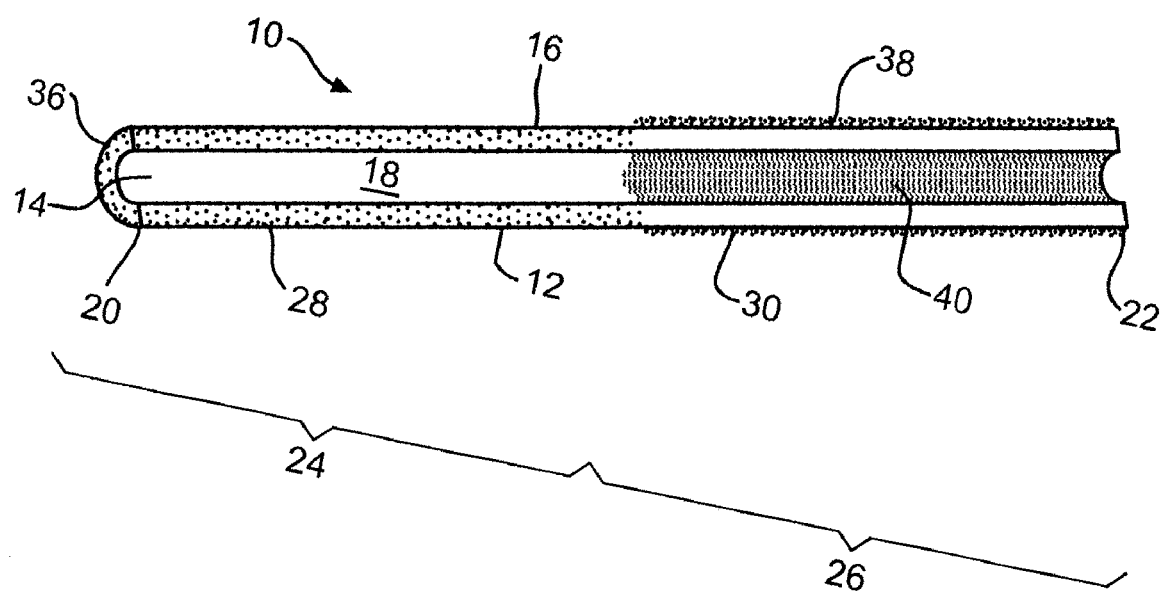
FIG. 10 is a cross-sectional view of a medical device according to an embodiment of the present invention.

FIG. 10 is a cross-sectional illustration of a medical device according to a preferred embodiment of the present invention. In this embodiment, the medical device comprises a cannula 10 having a main body 12 and defining a lumen 14. The cannula 10 has an exterior 16 and an interior surface 18. The cannula 10 has a first or distal end 20 and a second or proximal end 22, and a length extending between the two ends 20, 22. A first section 24 extends along a portion of the length, and a second section 26 extends along a different portion of the length. Each of the first 24 and second 26 sections preferably extends circumferentially around the cannula 10. A first therapeutic agent 28 comprises paclitaxel impregnated into the main body 12 of the first section 24. A second therapeutic agent 30 comprises a blend of rifampin and minocycline coated on the exterior 16 and interior 18 surfaces of the second section 26.

In one application medical devices according to the present invention can be used to establish access to a vessel within a body. As discussed above, medical devices according to preferred embodiments of the invention comprise cannulae that define a lumen. The distal end of the cannula can be interfaced with a vessel to establish a communicative passageway between the vessel and the lumen of the cannula. In this configuration, the medical device is particularly well suited for allowing convenient access to the vessel. These devices can be used advantageously in procedures that require repetitive access to the vessel, such as repetitive introduction of an agent into the blood stream or the repetitive extracorporeal treatment of blood, such as in hemodialysis procedures.

Figure 11:
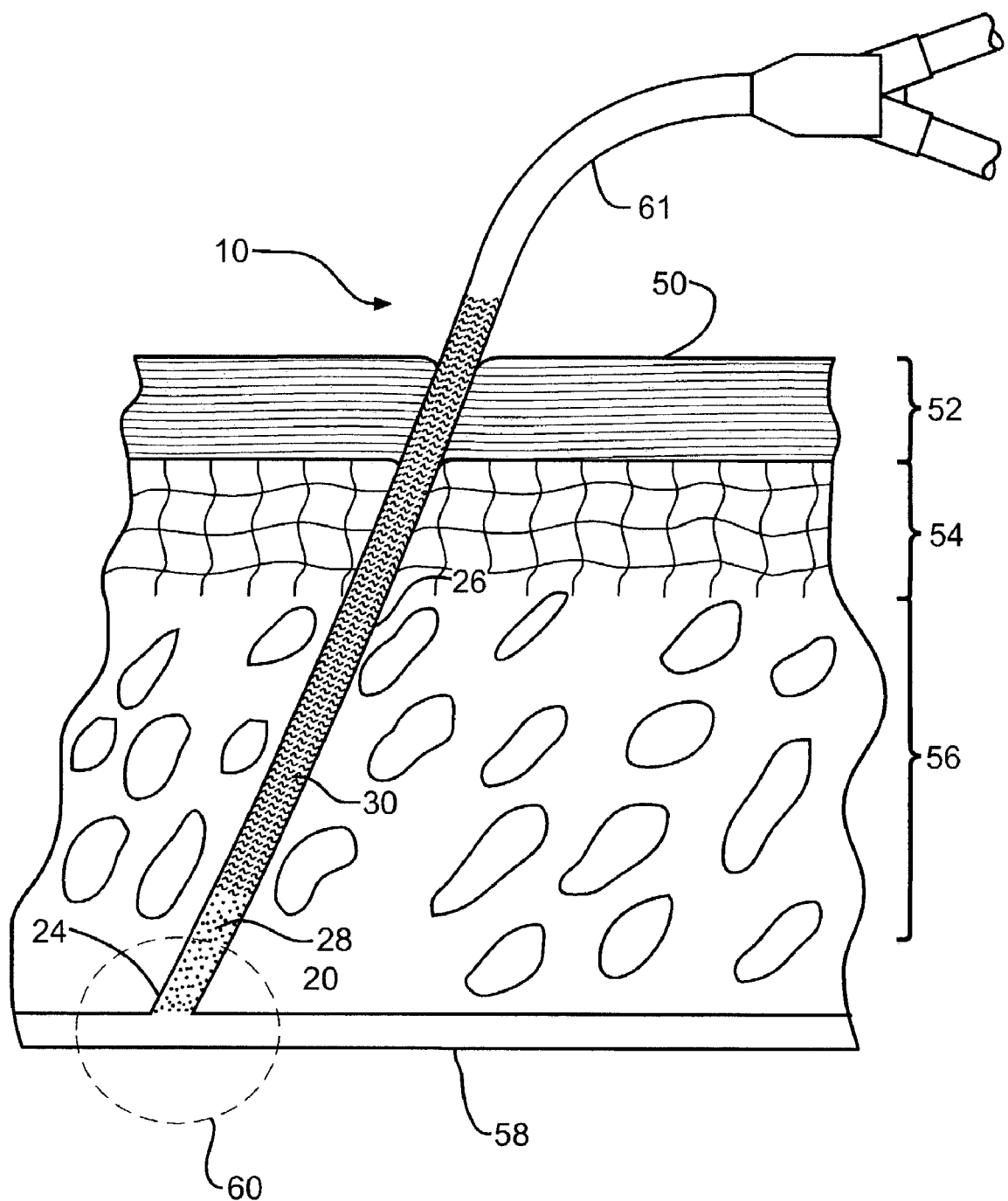
FIG. 11 is a schematic illustration of a medical device according to the present invention transcutaneously implanted into a body.

The medical devices according to the present invention can be completely implanted within the body, or only partially implanted within the body. In each scenario, however, at least a portion of the second section of the device remains within the subcutaneous space. FIG. 11 illustrates a schematic of a medical device 10 according to the present invention that is transcutaneously implanted into a body. In this embodiment, the medical device 10 traverses the skin through the epidermis 52, derma 54 and subcutaneous 56 layers to a vessel 58. An interface 60 is formed between the vessel 58 and the device 10. The interface defines a communicative passageway between the vessel 58 and the lumen of the device 10. The interface 60 can be a direct insertion of the distal end 20 of the device 10 into the vessel 58, or can comprise an attachment of the distal end 20 to the vessel 58, such as an anastomosis.

Because the device 10 is implanted transcutaneously, the device 10 in this embodiment includes a portion 61 that remains external to the body. This portion 61 provides the desired access to the lumen which is in communication with the vessel 58. Thus, in this embodiment, the vessel 58 can be accessed without further disruption to the skin 50.

The second section 26, which includes the second therapeutic agent 30, preferably is positioned across the subcutaneous layer 56. As illustrated in the FIGURES the second section 26 can extend beyond the subcutaneous layer and toward and through the derma 54 and epidermis 52. The first section 24, which includes the first therapeutic agent 28, preferably is positioned below the subcutaneous layer 56, and is preferably approximately adjacent the interface 60.

Figure 12:
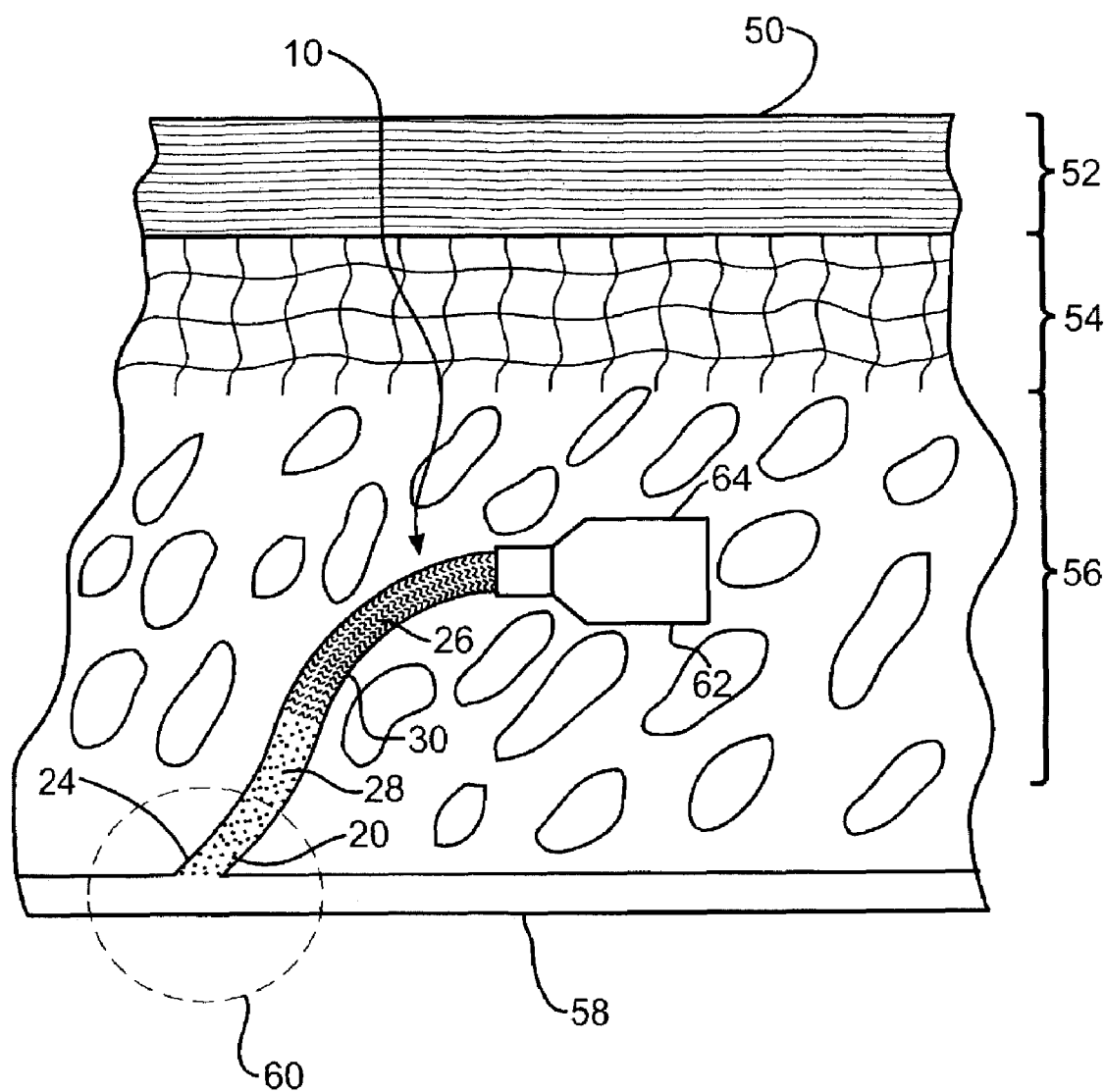
FIG. 12 is a schematic illustration of a medical device according to the present invention implanted subcutaneously into a body.

FIG. 12 illustrates a cannula 10 according to the present invention that is completely implanted within a body. In this embodiment, the cannula 10 includes an access port 62. The access port 62 defines a chamber that can receive a communicative member, such as a needle, for either withdrawing fluid from or directing fluid into the vessel 58. Typically, the access port 62 includes a section of resealable material 64 that prevents escape of fluid from the cannula 10 when a communicative member is not received by the access port 62. The resealable material can comprise silicon or any other suitable material.

In this embodiment, the second section 26, and therefore the second therapeutic agent 30, is completely contained within the subcutaneous layer 56. The first section 24, and therefore the first therapeutic agent 28, is positioned below the subcutaneous layer 56 and is preferably adjacent the interface 60 between the cannula 10 and the vessel 58.

Figure 13:
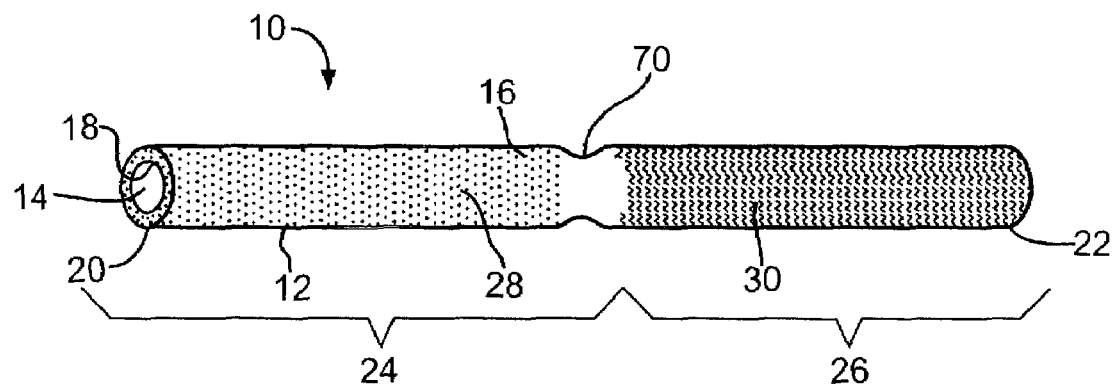
FIG. 13 is a schematic illustration of a medical device according to an embodiment of the present invention.

FIG. 13 illustrates another embodiment of the present invention. A medical device according to this embodiment is identical to the embodiment illustrated in FIG. 1, except as detailed below. Thus, the medical device of this embodiment comprises a cannula 10 that has a main body 12 and defines a lumen 14. The cannula 10 has an exterior surface 16, an interior surface 18, a first or distal end 20, and a second or proximal end 22. The cannula 10 has a length that extends from the first end 20 to the second end 22. A first section 24 extends along a portion of the length, and a second section 26 extends along a different portion of the length. Each of the first 24 and second 26 sections preferably extend circumferentially around the main body 12 of the cannula 10. A first therapeutic agent 28 is associated with the first section 24, and a second therapeutic agent 30 is associated with the second section 26.

The cannula 10 of this embodiment includes a separator 70 that spaces the first section 24 from the second section 26. The separator 70, in addition to physically separating the first 24 and second 26 sections, provides a visual indicator of the transition between these sections, which can aid fabrication and implantation procedures. The separator 70 can be any suitable separator that provides a separation between the first 24 and second 26 sections. The separator 70 need only not interfere with implantation in the body. Thus, as illustrated in FIG. 13, the separator 70 preferably comprises a portion of the main body 12 that has a reduced diameter as compared to the diameters of the first 24 and second 26 sections.

Examples of other suitable separators include markers, such as bands and dyes disposed within or on the main body 12 and other visual indicators. Also, the separator 70 can comprise an altered region of the main body 12, such as the reduced diameter section described above.

Figure 14:
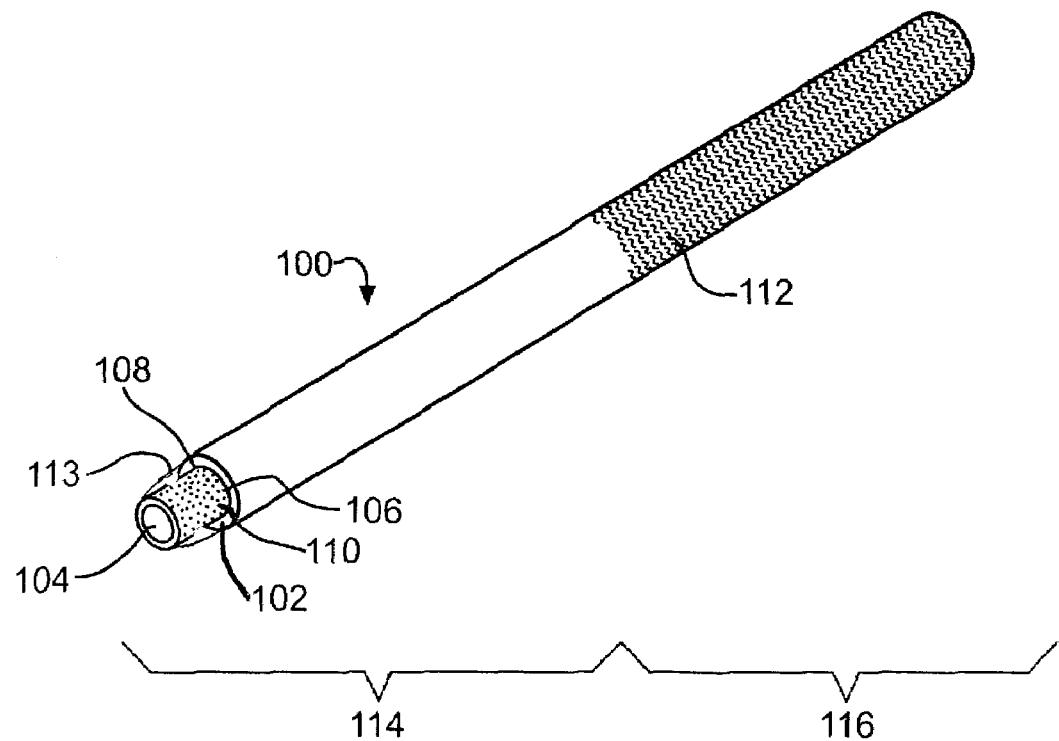
FIG. 14 is a schematic illustration of a medical device according to an embodiment of the present invention.

FIG. 14 illustrates a medical device according to another embodiment of the present invention. In this embodiment, the medical device comprises a cannula 100 and includes first 102 and second 104 tubes. The second tube 104 is positioned within a lumen 106 of the first tube 102. This configuration forms an annular space 108 between the interior surface of the first tube 102 and the exterior surface of the second tube 104. The first tube 102 can be formed of a porous material. In this embodiment, the first 110 and second 112 therapeutic agents are associated with the first 114 and second 116 sections along the length of the cannula 100. The first therapeutic agent 110 can be positioned within the annular space 108 between the tubes 102, 104. The second therapeutic agent 112 can be positioned within or on the first tube 102. The first therapeutic agent 110 escapes from the annular space 108 and through the main body of the first tube 102 due to its porous nature. A seal 113 can be positioned between a first end of the first tube 102 and a first end of the second tube 104 to prevent escape of the first therapeutic agent 110 directly from the annular space 108.

Figure 15:
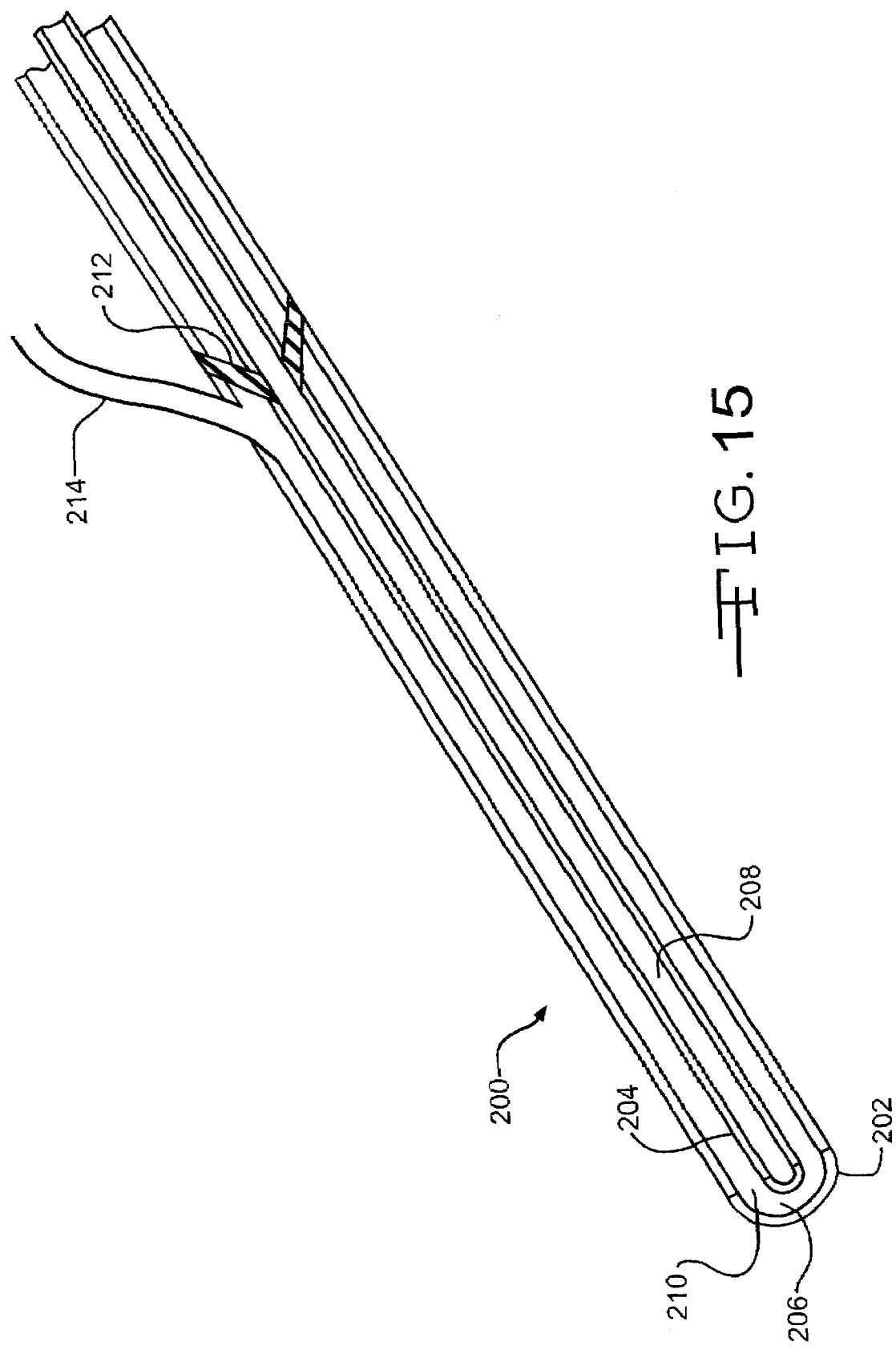
FIG. 15 is a schematic illustration of a medical device according to an embodiment of the invention.

FIG. 15 illustrates a medical device according to another embodiment of the present invention. The medical device according to this embodiment comprises a cannula 200 and includes first 202 and second 204 tubes. The second tube 204 is positioned within a lumen 206 of the first tube 202. The second tube 204 also defines a lumen 208. An annular space 210 is formed between the interior surface of the first tube 202 and the exterior surface of the second tube 204. An access line 214 provides communication with the annular space 210. A seal 212 is positioned proximal to the access line 214 and prevents fluid within the annular space 210 from moving up the cannula away from the body. In this embodiment, the first cannula 202 is preferably porous and the first therapeutic agent is preferably contained within the annular space 210 and escapes from the annular space 210 through the first tube 202 due to its porosity. The access line 214 allows for replacement of the first therapeutic agent that has escaped from the annular space 210 through the first tube 202. A seal (not illustrated) can close the annular space 210 at the distal end of the device 200 to prevent escape of the first therapeutic agent through the distal end. The second therapeutic agent can be placed in the annular space 210 proximal to the seal 212, thereby being separated from the first therapeutic agent. Similar to the first therapeutic agent, the second therapeutic agent will escape from the annular space 210 through the first tube 202 due to its porosity. Alternatively, the second therapeutic agent can be coated onto one or more surfaces of the first 202 and/or second 204 tubes. The lumen 208 of the second tube 204 is placed in communication with a body vessel. This double tube structure allows for the establishment of access to a body vessel and for the replenishment of the first therapeutic agent, which facilitates the use of the medical device as an indwelling cannula.

Figure 16:
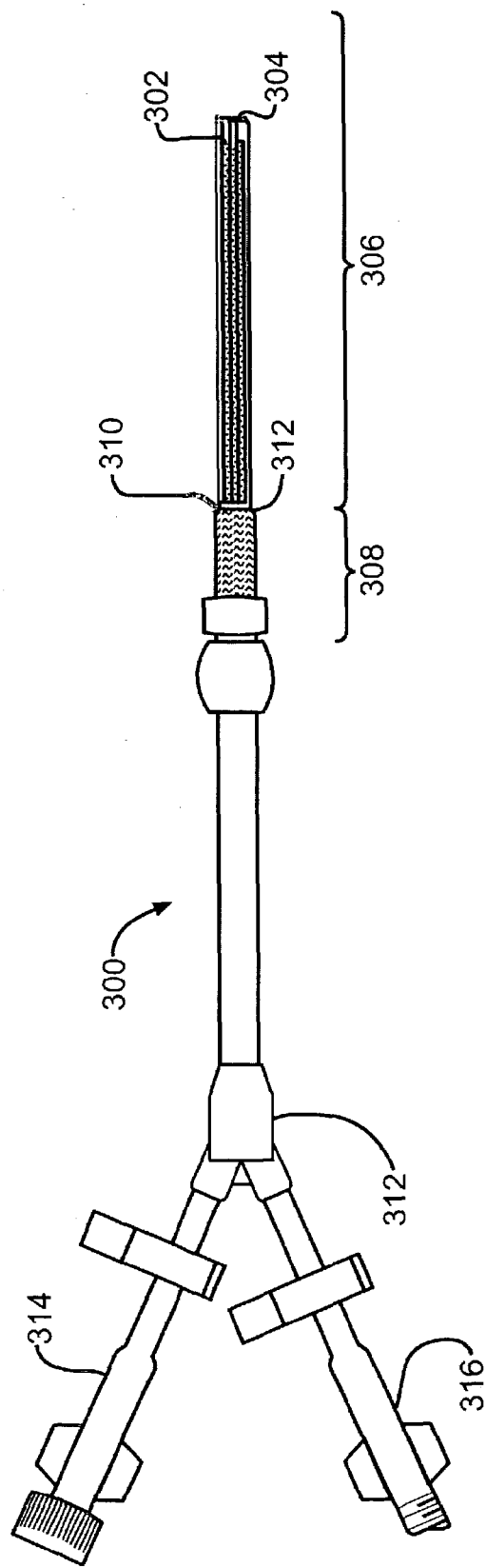
FIG. 16 is a schematic illustration of a medical device according to an embodiment of the invention.

FIG. 16 illustrates a medical device according to another embodiment of the invention. In this embodiment, the medical device comprises a catheter 300 that includes first 302 and second 304 lumens. A first section 306 of the catheter 300 is coated with paclitaxel, and a second section 308 is coated with a blend of rifampin and minocycline. In this embodiment, the separator 310 comprises a visual distinction between the first 306 and second 308 sections. Also, the separator 310 defines a slight increase in the diameter of the medical device. The separator 310 includes a taper 312 from the smaller diameter of the first section 306 to the larger diameter of the second section 308. The extracorporeal portion 312 of the catheter includes various connectors 314, 316 that are in individual communication with the first 302 and second 304 lumen, respectively.

The invention also includes medical devices having a single therapeutic agent. In these embodiments, the medical devices are preferably devices suitable for partial implantation in a body. Preferably, the devices have a therapeutic agent in or on a section of the device that will be implanted in the body. For example, a hemodialysis catheter can be coated with an antiproliferative agent, such as paclitaxel, along the portion of the device that will be implanted into the body. Alternatively, the therapeutic agent can be distributed within the material of the device in the section that will be implanted into the body. In these embodiments, no second therapeutic agent is utilized.

The first and second therapeutic agents can be associated with the respective portions of the medical device in any suitable manner. For example, if an agent(s) is bulk distributed in the material of the device, a swelling method can be utilized. Alternatively, the agent(s) can be added to a melt of bulk material. Once extruded, the device will include the agent(s) in the material. Also, if a coating layer is desired, the agent(s) can be dip-coated, spray-coated, or coated onto the device using any other suitable coating technique. Further, if different portions of the device have agents associated in different manners (e.g., bulk distribution versus coating layer), a combination of suitable techniques can be utilized. For example, Paclitaxel can be associated with a first portion by a swelling process, and rifampin/minocycline can be associated with a second portion of the device by a coating process. A separator between the first and second sections of devices according to these embodiments, as described above, can advantageously be used to isolate different techniques during fabrication.

EXAMPLES

Example 1

Loading of Silicone Tubing Devices with Paclitaxel

Silicon tubing segments (approximately 0.8 mm i.d., 1.7 mm O.D., 50 mm length, 120 mg weight) cut from silicone catheter samples (5FR single lumen) were swelled by soaking for approximately 20 hours in either freon or hexane. The samples were then loaded with paclitaxel by soaking for approximately 7 hours in one of the following solutions containing 4 mg/ml paclitaxel: 100% ethanol, 50/50% freon/ethanol, 50/50% hexane/ethanol. After loading, the tubing segments were allowed to dry for approximately 24 hours. The amount of paclitaxel loaded into each segment was determined by extracting the tubing in ethanol for approximately 12 hours, and assaying the extract by HPLC.

The results are summarized in Table I below:

| Sample Number | Original Swelling Solvent | Swelling Time (hr) | Paclitaxel Loading Solvent | Paclitaxel Loading Solution Concentration (mg/ml) | Loading Time (hr) | Drying Time (hr) | HPLC Measured Paclitaxel Mass Total (ug) | HPLC Measured Paclitaxel Mass per Length (ug/cm) |
|---|---|---|---|---|---|---|---|---|
| 1 | Freon | ~20 | 100% Ethanol | 4 | ~7 | ~24 | 44 | 8.8 |
| 2 | Freon | ~20 | 100% Ethanol | 4 | ~7 | ~24 | 48 | 9.5 |
| 3 | Freon | ~20 | 50% Freon/Ethanol | 4 | ~7 | ~24 | 94 | 18.7 |
| 4 | Freon | ~20 | 50% Freon/Ethanol | 4 | ~7 | ~24 | 76 | 15.3 |
| 7 | Hexane | ~20 | 100% Ethanol | 4 | ~7 | ~24 | 55 | 11.0 |
| 8 | Hexane | ~20 | 100% Ethanol | 4 | ~7 | ~24 | 34 | 6.8 |
| 9 | Hexane | ~20 | 50% Hexane/Ethanol | 4 | ~7 | ~24 | 66 | 13.2 |
| 12 | Hexane | ~20 | 50% Hexane/Ethanol | 4 | ~7 | ~24 | 71 | 14.1 |
| | | | | | | AVG | 61 | 12 |
| | | | | | | STDS | 19 | 4 |

On average the tubing segments yielded approximately 61±19 μg paclitaxel. For comparison, 3.0 mm×15 mm long VFlexPlus coronary stents, which appeared effective in inhibiting restonosis in clinical trial studies, were loaded with approximately 60 μg paclitaxel.

All references cited herein, including all U.S. patents and other cited references, are hereby incorporated into this disclosure in their entirety.

The invention claimed is:

1. A medical device for at least partial implantation, comprising:
   a main body having a first end, a second end, and a lumen extending therebetween,
   a first section proximal the first end of said main body and having a first therapeutic agent, said first therapeutic agent comprising one or more members selected from the group consisting of antiproliferatives, anticoagulants, antithrombotics, thrombolytics, and fibrinolytics; and
   a second section proximal the second end of said main body and having a second therapeutic agent, said second therapeutic agent comprising an antimicrobial;
   said main body having a length such that when said device is at least partially implanted said first end accesses a body vessel and at least a portion of said second section is disposed within a subcutaneous space of a patient.

2. The medical device of claim 1, wherein the main body comprises a cannula.

3. The medical device of claim 1, wherein the first therapeutic agent comprises an antiproliferative.

4. The medical device of claim 3, wherein the antiproliferative comprises paclitaxel.

5. The medical device of claim 1, wherein the antimicrobial is a member selected from the group consisting of antibiotics, antiseptics, and disinfectants.

6. The medical device of claim 5, wherein the antimicrobial is an antibiotic.

7. The medical device of claim 6, wherein the antibiotic is one or more members selected from the group consisting of tetracyclines, rifamycins, macrolides, penicillins, cephalosporins, other beta-lactam antibiotics, aminoglycosides, chloramphenicol, sufonamides, glycopeptides, quinolones, fusidic acid, trimethoprim, metronidazole, clindamycin, mupirocin, polyenes, azoles and beta-lactam inhibitors.

8. The medical device of claim 6, wherein the antibiotic comprises a combination of rifampin and minocycline.

9. The medical device of claim 1, wherein the main body has an exterior surface, the first therapeutic agent is impregnated within the first section, and the second therapeutic agent is posited on the exterior surface of the second section.

10. The medical device of claim 1, further comprising a separator spacing the first section from the second section.

11. The medical device of claim 10, wherein the separator comprises a portion of the main body having a reduced diameter.

12. The medical device of claim 10, wherein the separator comprises a band surrounding the main body.

13. The medical device of claim 10, wherein the separator comprises a dye disposed in or on the main body.

14. A medical device for at least partial implantation comprising:
   a cannula having first and second ends, interior and exterior surfaces, and defining a lumen;
   a first axial section proximal the first end having a first therapeutic agent;
   a second axial section proximal the second end having a second therapeutic agent; and
   a separator spacing the first axial section from the second axial section.

15. The medical device of claim 14, wherein the first therapeutic agent is impregnated within the first section, and the second therapeutic agent is posited on one of the interior and exterior surfaces of the second section.

16. The medical device of claim 14, wherein the first therapeutic agent is impregnated within the first section, and the second therapeutic agent is posited on the interior surface and the exterior surface of the second section.

17. A cannula for use in the extracorporeal treatment of a bodily fluid of a patient, comprising:
   a main body having first and second ends, interior and exterior surfaces, and defining a lumen;
   a first section proximal the first end;
   a second section proximal the second end; said main body sized such that during said extracorporeal treatment said first end accesses a target body vessel carrying said bodily fluid and at least a portion of said second section is positioned within a subcutaneous layer in the body of the patient;

an antiproliferative impregnated within the first section; and an antimicrobial coated on at least one of the interior and exterior surfaces of the second section.

18. A method of establishing access to a vessel of a body, comprising:
 providing a medical device comprising a cannula having a distal end, a proximal end, an interior surface, an exterior surface, and defining a lumen, the cannula further having a length extending from the proximal end to the distal end, a first section generally adjacent the distal end with a first therapeutic agent extending along part of the length, and a second section generally adjacent the proximal end with a second therapeutic agent extending along part of the length, said first therapeutic agent comprising one or more members selected from the group consisting of antiproliferatives, anticoagulants, antithrombotics, thrombolytics, and fibrinolytics, and said second therapeutic agent comprising an antimicrobial;
 implanting the distal end into the body; and
 forming an interface between the distal end and the vessel.

19. The medical device of claim 18, wherein the implanting the distal end comprises positioning the first section below a subcutaneous layer of the body.

20. The medical device of claim 19, wherein the implanting the distal end further comprises positioning the second section comprising the second therapeutic agent across a subcutaneous layer of the body.

21. The medical device of claim 19, wherein the implanting the distal end further comprises positioning the second section comprising the second therapeutic agent within a subcutaneous layer of the body.

22. A medical device for at least partial implantation, comprising:
 a main body having a first end, a second end, and a length extending from the first end to the second end;
 a first axial section along the length having a first therapeutic agent comprising one or more members selected from the group consisting of antiproliferatives, anticoagulants, antithrombotics, thrombolytics, and fibrinolytics;
 a second axial section along the length having a second therapeutic agent, said second axial section distinct from said axial first section, and
 a separator for spacing said second axial section from said first axial section.

* * * * *